(12) United States Patent
Del Soldato

(10) Patent No.: US 6,218,417 B1
(45) Date of Patent: Apr. 17, 2001

(54) ACE-INHIBITOR NITRIC SALTS

(75) Inventor: Piero Del Soldato, Milan (IT)

(73) Assignee: Nicox, S.A., Paris (FR)

( * ) Notice: Subject to any disclaimer, the term of this patent is extended or adjusted under 35 U.S.C. 154(b) by 0 days.

(21) Appl. No.: 09/423,287

(22) PCT Filed: Jun. 24, 1998

(86) PCT No.: PCT/EP98/03946

§ 371 Date: Nov. 8, 1999

§ 102(e) Date: Nov. 8, 1999

(87) PCT Pub. No.: WO99/00361

PCT Pub. Date: Jan. 7, 1999

(30) Foreign Application Priority Data

Jun. 27, 1997 (IT) ............................................. MI97A01523

(51) Int. Cl.⁷ ..................... A61K 31/403; A61K 31/407; A61K 31/4166; C07D 495/10; C07D 233/32
(52) U.S. Cl. ......................... 514/398; 514/409; 514/412; 514/423; 548/409; 548/322.5; 548/492; 548/533
(58) Field of Search .................... 548/533, 409, 548/492, 322.5; 514/423, 409, 412, 398

(56) References Cited

U.S. PATENT DOCUMENTS 5,625,083   4/1997   Bezuglov et al. .................... 549/467

FOREIGN PATENT DOCUMENTS

| 0 357581 | 3/1990 | (EP) . |
| 94 06433 | 3/1994 | (WO) . |
| 94 10141 | 5/1994 | (WO) . |
| 95 30641 | 11/1995 | (WO) . |

OTHER PUBLICATIONS

Laubie et al., "Inhibition of Angiotensin I–Converting Enzyme with S 9490: Biochemical Effects, Interspecies Differences, and Role of Sodium Diet in Hemodynamic Effects", *Journal of Cardiovascular Pharmacology*, pp. 1076–1081, (1984), vol. 6, No. 6.

Subissi et al., "Angiotensin converting enzyme inhibitors potentiate the bronchoconstriction induced by substance P in the guinea–pig". *Br. J. Pharmacol*, (1990), 100, pp. 502–506.

J.F. Pinon, "In Vivo Study of Platelet Aggregation in Rats" *Journal of Pharmacmacological Methods* 12, pp. 79–84 (1984).

Konzett, Arch. Exp. Pathol. Pharmacol, 195, 71, (1984).

*Primary Examiner*—Laura L. Stockton
(74) *Attorney, Agent, or Firm*—Arent, Fox, Kintner, Plotkin & Kahn

(57) ABSTRACT

Compounds having platelet anti-aggregating activity and antihypertension activity having reduced branchial side effects.

9 Claims, No Drawings

ACE-INHIBITOR NITRIC SALTS

This application is a 371 of PCT/EP98/03946 filed Jun. 24, 1998.

The present invention relates to products having an antihypertensive activity combined with a platelet-antiaggregating activity, and pharmaceutical compositions thereof.

In particular, it relates to products having an improved antihypertensive activity and fewer side effecs, in particular in the bronchi, compared to the products currently being marketed as antihypertensive agents. The antihypertensive activity is combined with a platelet-antiaggregating activity.

Antihypertensive agents are known in the art. Particularly known are ACE inhibitors, which represent a first-choice pharmacological measure in the treatment of cardiovascular diseases such as hypertension, angina, myocardial ischaemia, congestive heart failure, and others. ACE inhibitors act on the renin-angiotensin system which releases angiotensin II, one of the most effective hypertensive agents known. More precisely, these drugs inhibit the activity of the angiotensin converting enzyme, a carboxypeptidase which is mostly present in lungs, kidneys, and vessels. The action of this enzyme is not specific. It inactivates plasma bradykinin, which possesses a vasodilatatory activity, and also helps diuresis and, in particular, natriuresis. In other terms, plasma bradykinin possesses opposite effects compared to those of angiotensin II. Therefore, ACE inhibitors prevent formation of angiotensine II and, at the same time, degradation of bradykinin. Hence, ACE inhibitors certainly represent one of the most significant pharmacological innovation of the past few decades.

However, the administration of ACE inhibitors is often (about 20 to 30% of the cases) accompanied by side effects in the respiratory system, such as cough, dyspnea, bronchoconstriction. Furthermore, these drugs show a rather limited therapeutic profile, for example they have no platelet-antiaggregating activity, so that, in the above cardiovascular treatments, they are often associated with other drugs having an antiaggregating activity. For example, in the treatment of myocardial infarction and prevention of relapses, it is essential to use a multiple cardiovascular therapy including, among others, the association of an antihypertensive with an antiaggregating agent.

It was felt the need for drugs with a better therapeutic profile and fewer side effects, in particular, at the respiratory system, for example the bronchi.

The Applicant has unexpectedly and surprisingly found a specific class of ACE-inhibitor salts characterised by the fact that they possess, compared to other salts of the same compounds, a better antihypertensive activity and have fewer side effects in the bronchi.

An object of the present invention is, therefore, the nitric salts of ACE inhibitors having the following formulas:

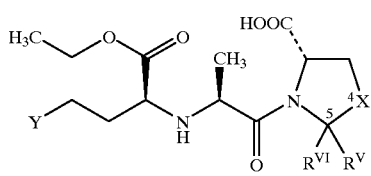
(I)

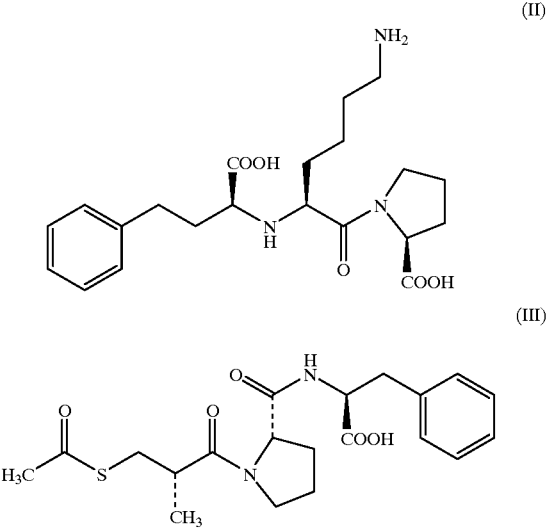

in formula

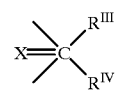
(I)

or N—CH$_3$;
Y=CH$_3$, phenyl;
R$^{III}$=H,
R$^{III}$ together with R$^{IV}$ forms the following ring in the carbon at position 4

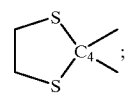
(IVa)

R$^{III}$ together with R$^V$ (carbons at positions 4 and 5) forms the cyclohexane or cyclopentane rings

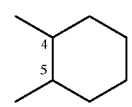
(IIIa)

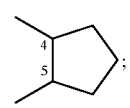
(IIIb)

R$^{IV}$=H, or R$^{IV}$ forms with R$^{III}$ ring (IVa);
R$^V$=H, or a free valence, or R$^V$ forms with R$^{III}$ rings (IIIa) or (IIIb);
R$^{VI}$=H, or a single bond —O when R$^V$ is a free valence so as to form a ketone group with the carbon atom at position 5.

The preferred nitrate salts of formula (I) include:
when X=C (R$^{III}$) (R$^{IV}$) as above defined, Y=phenyl, R$^{III}$=R$^{IV}$=R$^V$=R$^{VI}$=H, the residue of Enalapril;

as in Enalapril but with $R^{III}$ which, together with $R^{IV}$, forms ring (IVa), the residue of Spirapril;
as in Enalapril but with $R^{III}$ which, together with $R^V$, forms ring (IIIb), the residue of Ramipril;
as in Enalapril but with Y=$CH_3$ and $R^{III}$ which, together with $R^V$, forms ring (IIIa), the residue of Perindopril;
as in Enalapril, but with X=N—$CH_3$, $R^V$ is a free valence and $R^{VI}$=—O so as to form with carbon atom $C_5$ a ketone group, the residue of Imidapril.

The compounds of the classes of the invention, which are the precursors of the salts, are used as optically-active single isomers or as mixtures thereof or in the form of racemates.

The precursor of class II is known as Lisinopril, that of class III is known as Alacepril. The precursors are prepared according to the methods described in "The Mercx Index, Ed. 12", herein incorporated by reference.

The salts of the present invention are prepared according to the following method. The substance to be salified is dissolved in an organic solvent, not containing in the molecule free hydroxyl groups, and then a stoichiometric amount of concentrated nitric acid is added. The salt is recovered by filtration and washed several times with a solvent, for example that used in the reaction. Polar organic solvents are preferred, such as , for example, acetonitrile, ethyl acetate, and others.

It has surprisingly been found that the compounds of the present invention improve, compared to the same substances and ACE salts generally, the pharmacological profile of the above ACE inhibitors and, additionally, exhibit a more favourable general and regional tolerability.

The compounds of the present invention can be used as cardiovascular drugs, in particular in the treatnent of hypertension, angina, myocardial ischaemia, congestive heart failure.

The salts of the present invention are formulated in the correspomding pharmaceutical compositions according to the methods well known to those skilled in the art, which are, for example, described in Remington's Pharmaceutical Sciences, Ed. 15.

The examples below are meant to describe the invention and should not be understood as a limitation of same.

EXAMPLE 1

Synthesis of (S)-1-[N-[1-(ethoxycarbonyl)-3-phenylpropyl]-L-alanyl]-L-proline (Enalapril), and obtainement of the nitrate salt in acetonitrile A mixture of ethyl-2-oxo-4-phenylbutyrate (2.1 g) and L-alanyl-L-proline (0.4 g) in ethanol/water 1/1 was treated slowly at room temperature with a solution of sodium cyanoborohydride (0.4 g) in ethanol/water 1/1.

At the end of the reaction, the product was absorbed on a strong acid ion exchange resin and eluted with an aqueous solution containing 2% (v/v) of pyridine. The fractions which contained the product were lyophilised to obtain the crude compound. Chromatography then allowed isolation of the desired isomer (−) practically pure (0.24 g).

The isomer was then dissolved in acetonitrile and treated, maintaining the reactor in an ice bath, with a stoichiometric amount of concentrated nitric acid dissolved in acetonitrile. After cooling and filtration, the solid was washed with cold acetonitrile and a 97%-pure (HPLC: high pressure liquid chromatography) Enalapril nitric salt was recovered. A 99%-pure (HPLC) salt could be obtained by crystallisation from acetonitrile.

EXAMPLE 2

Synthesis of Enalapril, and Obtainement of the Nitrate Salt in Ethyl Acetate

A mixture of ethyl-2-oxo-4-phenylbutyrate (15 g), L-alanyl-L-proline (9 g), molecular sieves 3 A° (40 g) and Raney nickel (10.8 g) in ethanol (300 ml) was hydrogenated at room temperature and at a pressure of about 3 atm. up to the hydrogen is not-consumed any more. After filtration of the undissolved substance (washing well with ethanol, the solvent was evaporated under vacuunm to obtain a mixture of diastereoisomers formed of 85% by the expected product (by HPLC). The obtained product was dissolved in a mixture made up of 200 ml of water and 70 ml of methyl acetate. By keeping the solution under stirring, the pH was adjusted to 8.6 with 50% NaOH. The organic phase was separated and the aqueous phase was thoroughly washed with ethyl acetate (3×50 ml). The aqueous phase was adjusted to pH 4.3 with hydrochloric acid, saturated with sodium chloride and then extracted with ethyl acetate (4×100 ml). After drying with sodium sulphate and evaporating the solvent off under vacuum, the residue was dissolved in ethyl acetate maintaining the reactor in an ice bath, and salified by treating with a stoichiometric amount of concentrated nitric acid. After stirring for two hours, it was cooled, filtered, washed with ethyl acetate and recrystallised from acetonitrile to obtain 12.5 g of nitric salt of the isomer (−), about 99%-pure (by HPLC).

EXAMPLE 3

Acute Toxicity

A group of 10 mice (weight 15 to 25 g) received a single oral dose of 100 mg/Kg. All the animals survived during the observation period (14 days). No toxicity symptom was observed.

EXAMPLE 4

Antihypertensive Activity

The antihypertensive activity of the nitrate salts of the compounds of the invention was determined in accordance with the method of Laubie et al., J. Cardiovasc. Pharmacol. 6, 1076, 1984. No 6 rats weighing about 200 to 250 g were used per experimental group. Four groups were formed, which were intraperitoneally treated respectively as shown below:

| | |
|---|---|
| Enalapril maleate | 100 µg/Kg |
| Enalapril maleate | 300 µg/Kg |
| Enalapril nitrate | 100 µg/kg |
| Enalapril nitrate | 300 µg/kg |

The doses are referred to the amount of Enalapril (cation) in the salt. The antihypertensive response was evaluated as per-cent inhibition of the hypertension induced by the administration of a dose of 100 µg/Kg i.v. of angiotensin I as described in the above article.

The results are shown in Table I

TABLE I

| COMPOUND | DOSE (µg/Kg/i.p.) | Inhibition % for angiotensin-I-induced hypertension |
|---|---|---|
| Enalapril maleate | 100 | 18 |
| Enalapril maleate | 300 | 55 |
| Enalapril nitrate | 100 | 35 |
| Enalapril nitrate | 300 | 67 |

EXAMPLE 5

Pharmacological Effects of the Salts of the Invention on Bronchial Spasm Induced by Administration of Substance P Activity was evaluated measuring the strengthening of bronchial spasm induced by substance P, determined in accordance with the method of Subissi et al., Br. J. Pharmacol. 100, 502–6, 1990. The model described by Subissi is predictive of bronchial side effects due to the administration of ACE inhibitors.

Four groups (6 animals/group) of female Guinea pigs weighing about 300 to 400 g were anaesthetised with ethyl urethane (200 mg/Kg) under artificial pressure at constant positive pressure. The compounds were administered intraperitoneally 30 minutes before substance P. The salt doses administered were the same as in Example 4. The changes in tidal air were then measured in accordance wuth the method of Konzett, Arch. Exp. Pathol. Pharmacol. 195, 71, 1940, before and after the administration of substance P (200 $\mu$g/Kg), with or without the test salts, i.e. Enalapril maleate and nitrate.

The results are shown in Table II

As seen from the data, Enalapril nitrate possessed a better respiratory profile than Enalapril maleate at both tested doses.

TABLE II

| COMPOUND | DOSE ($\mu$g/Kg/i.p.) | Tidal air change % in bronchial spasm induced by substance P |
|---|---|---|
| Enalapril maleate | 100 | +16 |
| Enalapril maleate | 300 | +28 |
| Enalapril nitrate | 100 | −5 |
| Enalapril nitrate | 300 | −7 |

EXAMPLE 6

Platelet-antiaggregating Activity

The in-vivo model described by Pinon et al., J. Pharm. Methods 12, 79–84, 1984, was used.

Two groups of 6 rats each, weighing about 200 to 250 g, were treated with an oral. dose of 10 mg/Kg/die of Enalapril maleate or nitrate respectively (the dose is referred to the amount of Enalapril cation in the salt) for five days, while a third group acted as a control group. About 18 hours before the last treatment, the animals were fasted. One hour after this treatment the animals were anaesthetised with 10% ethyl urethane (1 g/Kg intraperitoneally) and the left jugular vein and the right carotid artery were cannulated. Collagen (type 6, Sigma) was then administered intravenously at a dose of 2 mg/Kg. Three minutes later two blood samples, A and B, were collected from the carotid artery of each animal.

1.6 ml of EDTA/formalin buffer (24 mM tetrasodium EDTA, 1.3 mM $KH_2PO_4$, 13.4 mM $Na_2HPO_4$) was added to the first sample (sample A) containing 0.4 ml of blood.

The second blood sample (sample B) had the same volume as the previous sample (0.4 ml of blood) but, instead of the buffer, 1.6 ml of a saline solution (physiological NaCl solution) was added.

The samples were then transferred into 5-ml test tubes and allowed to stand at room temperature for 15 minutes.

A microscope platelet count was then performed. The platelet count in samples B and A represent the total number of platelets and the total number of aggregated platelets respectively. The results shown in Table III are expressed as a % of platelet aggregation and are referred to the % value obtained in the control group.

TABLE III

| COMPOUND | DOSE/die (mg/Kg/os) | Antiaggregating activity % |
|---|---|---|
| Enalapril maleate | 10 | 5 |
| Enalapril nitrate | 10 | 58 |

What is claimed is:

1. Nitric salts of ACE inhibitors having the following formulas:

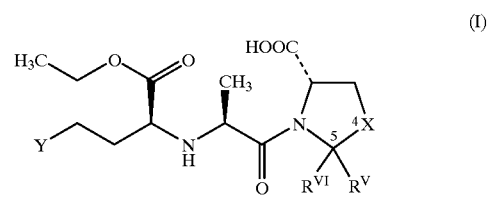

(I)

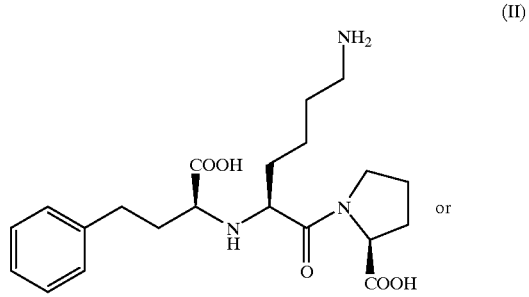

(II)

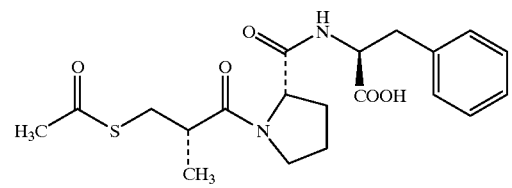

(III)

in formula

(I)

or N—CH$_3$

Y=CH$_3$, or phenyl;

R$^{III}$=H,

R$^{III}$ together with R$^{IV}$ forms the following ring in the carbon at position 4

(IVa)

R$^{III}$ together with R$^V$ (carbons at positions 4 and 5) forms the cyclohexane or cyclopentane rings

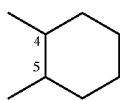 (IIIa)

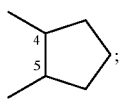 (IIIb)

$R^{IV}$=H, or $R^{IV}$ forms with $R^{III}$ ring (IVa);

$R^V$=H, or a free valence or $R^V$ forms with $R^{III}$ rings (IIIa) or (IIIb);

$R^{VI}$=H, or a single bond —O when $R^V$ is a free valence so as to form a ketone group with the carbon atom at position 5.

2. Nitric salts according to claim 1, wherein, in formula (I), X=C ($R^{III}$) ($R^{IV}$), Y=phenyl, $R^{III}$=$R^{IV}$=$R^V$=$R^{VI}$=H, the residue of Enalapril;

as in Enalapril but with $R^{III}$ which, together with $R^{IV}$, forms ring (IVa), the residue of Spirapril;

as in Enalapril but with $R^{III}$ which, together with $R^V$, forms ring (IIIb), the residue of Ramipril;

as in Enalapril but with Y=$CH_3$ and $R^{III}$ which, together with $R^V$, forms ring (IIIa), the residue of Perindopril;

as in Enalapril, but with X=N—$CH_3$, $R^V$ is a free valence and $R^{VI}$=—O so as to form with carbon atom $C_5$ a ketone group, the residue of Imidapril.

3. Nitric salts according to claim 2, wherein, in formula (I), X=C ($R^{III}$) ($R^{IV}$), Y=phenyl, $R^{III}$=$R^{IV}$=$R^V$=$R^{VI}$=H, the residue of Enalapril.

4. A pharmaceutical composition containing an effective amount of one or more nitrate salts of compounds I, II or III of claim 1 and a pharmaceutically acceptable excipient or carrier.

5. A method of treating hypertension in an individual comprising administering a therapeutically effective amount of compounds I, II or III according to claim 1.

6. A method for treating a patient in need of a platelet antiaggregating treatment comprising administering to said patient an effective amount of compounds I, II or III according to claim 1.

7. A method for treating angina in an individual comprising administering a therapeutically effective amount of compounds I, II or III according to claim 1.

8. A method for treating myocardial ischaemia in an individual comprising administering a therapeutically effective amount of compounds I, II or III according to claim 1.

9. A method for treating congestive heart failure in an individual comprising administering a therapeutically effective amount of compounds I, II or III according to claim 1.

* * * * *